US008193134B2

(12) United States Patent
Chuah et al.

(10) Patent No.: US 8,193,134 B2
(45) Date of Patent: *Jun. 5, 2012

(54) THICKENED SPREADABLE WARMING LUBRICANT

(75) Inventors: Beng Sim Chuah, Petaling Jaya (MY); David M. Lucas, Petaling Jaya (MY); Tsui Shih Yeun, Puchong (MY); Dave Narasimhan, Flemington, NJ (US)

(73) Assignee: Ansell Healthcare Products LLC, Red Bank, NJ (US)

( * ) Notice: Subject to any disclaimer, the term of this patent is extended or adjusted under 35 U.S.C. 154(b) by 68 days.

This patent is subject to a terminal disclaimer.

(21) Appl. No.: 12/716,786

(22) Filed: Mar. 3, 2010

(65) Prior Publication Data

US 2010/0160457 A1    Jun. 24, 2010

Related U.S. Application Data

(63) Continuation of application No. 11/064,284, filed on Feb. 23, 2005, now Pat. No. 7,709,428.

(51) Int. Cl.
*C10M 169/04* (2006.01)
*C10M 129/04* (2006.01)

(52) U.S. Cl. .................... 508/583; 508/501; 508/591

(58) Field of Classification Search .................. 508/583, 508/591, 501
See application file for complete search history.

(56) References Cited

U.S. PATENT DOCUMENTS

| | | | |
|---|---|---|---|
| 4,754,404 A | 6/1988 | Inoue | |
| 4,851,434 A | 7/1989 | Deckner | |
| 4,930,522 A | 6/1990 | Busnel et al. | |
| 4,952,560 A | 8/1990 | Kigasawa et al. | |
| 4,983,404 A | 1/1991 | Raman et al. | |
| 5,024,852 A | 6/1991 | Busnel et al. | |
| 5,097,697 A | 3/1992 | Carnal et al. | |
| 5,323,544 A | 6/1994 | Osgood | |
| 5,441,723 A | 8/1995 | Simmons | |
| 5,512,289 A | 4/1996 | Tseng et al. | |
| 5,514,698 A | 5/1996 | Ahmad et al. | |
| 5,549,924 A | 8/1996 | Shlenker et al. | |
| 5,592,949 A * | 1/1997 | Moench et al. | 128/837 |
| 5,649,825 A | 7/1997 | Ratkus | |
| 5,885,591 A | 3/1999 | Ahmad et al. | |
| 5,888,441 A | 3/1999 | Milner | |
| 5,922,336 A | 7/1999 | Tebbe | |
| 5,977,223 A | 11/1999 | Ryan et al. | |
| 5,985,860 A | 11/1999 | Toppo | |
| 6,007,836 A | 12/1999 | Denzer | |
| 6,075,081 A | 6/2000 | Nile et al. | |
| 6,139,848 A | 10/2000 | Ahmad et al. | |
| 6,196,227 B1 | 3/2001 | Tsushima | |
| 6,211,081 B1 | 4/2001 | Mikata | |
| 6,290,981 B1 | 9/2001 | Keefer | |
| 6,306,514 B1 | 10/2001 | Weikel et al. | |
| 6,347,409 B1 | 2/2002 | Nile et al. | |
| 6,352,666 B1 | 3/2002 | Nile et al. | |
| 6,378,137 B1 | 4/2002 | Hassan et al. | |
| 6,428,791 B1 | 8/2002 | Lezdey et al. | |
| 6,541,030 B2 | 4/2003 | Vaghefi | |
| 6,551,608 B2 | 4/2003 | Yao | |
| 6,620,942 B2 | 9/2003 | Yeh et al. | |
| 6,664,296 B1 | 12/2003 | Meignant | |
| 6,709,725 B1 | 3/2004 | Lai et al. | |
| 6,840,244 B2 | 1/2005 | Kemp | |
| 7,005,408 B2 | 2/2006 | Ahmad et al. | |
| 7,037,579 B2 | 5/2006 | Hassan et al. | |
| 7,064,114 B2 | 6/2006 | Yiv et al. | |
| 7,084,884 B1 | 8/2006 | Nelson | |
| 7,157,393 B2 | 1/2007 | Gromelski et al. | |
| 7,176,238 B1 | 2/2007 | Garvey et al. | |
| 7,214,390 B2 | 5/2007 | Barone, Jr. et al. | |
| 7,285,517 B2 | 10/2007 | Ahmad et al. | |
| 7,405,186 B2 | 7/2008 | Harrison | |
| 7,417,013 B2 | 8/2008 | Ahmad et al. | |
| 7,709,428 B2 * | 5/2010 | Chuah et al. | 508/583 |
| 2001/0039380 A1 | 11/2001 | Larson et al. | |
| 2002/0103414 A1 | 8/2002 | Harrison et al. | |
| 2002/0176892 A1 | 11/2002 | Drizen et al. | |
| 2002/0192375 A1 | 12/2002 | Sun et al. | |
| 2003/0207772 A1 | 11/2003 | Ahmad et al. | |
| 2003/0211161 A1 | 11/2003 | Ahmad et al. | |
| 2003/0232090 A1 | 12/2003 | Ahmad et al. | |
| 2004/0009227 A1 | 1/2004 | Yao | |
| 2004/0037911 A1 | 2/2004 | Letourneau et al. | |

(Continued)

FOREIGN PATENT DOCUMENTS

| | | |
|---|---|---|
| EP | 0636374 | 2/1995 |
| JP | 2292212 | 12/1990 |
| JP | 2003183115 | 7/2003 |
| WO | WO-93/18740 | 9/1993 |
| WO | WO-03/092650 A1 | 11/2003 |
| WO | WO-03/092651 | 11/2003 |
| WO | WO-03/092652 A1 | 11/2003 |
| WO | WO-2005/081952 A2 | 9/2005 |

OTHER PUBLICATIONS

PCT/US2005/009877 International Search Report, dated Feb. 1, 2006, 3 pgs.
PCT/US2005/009877 Written Opinion, dated Feb. 1, 2006, 4 pgs.
Final Office Action in U.S. Appl. No. 11/063,711 dated Sep. 22, 2008, 10 pgs.
Non-Final Office Action in U.S. Appl. No. 11/063,711 (May 1, 2009),14 pgs.
Non-Final Office Action in U.S. Appl. No. 11/063,711, (Oct. 30, 2009), 11 pgs.

*Primary Examiner* — Jim Goloboy
(74) *Attorney, Agent, or Firm* — Moser Taboada

(57) ABSTRACT

A substantially anhydrous, thickened, spreadable, warming lubricant composition comprising a mixture of glycerin, polyhydric alcohol, a non-ionic surfactant, and a Carbomer thickener, the surfactant improving wetting and spreadability of the composition on skin and latex, and the thickener providing a creamy rich feel to the composition, such that the composition can be applied to skin or a condom and provide an optimal warming effect upon contact with ambient moisture during use and such that the composition can be added to a condom package and, over the course of a week, spread and coat nearly the entire internal and external surfaces of the condom.

20 Claims, No Drawings

U.S. PATENT DOCUMENTS

| | | |
|---|---|---|
| 2004/0055094 A1 | 3/2004 | Massoni |
| 2004/0086575 A1 | 5/2004 | Smith |
| 2004/0115250 A1 | 6/2004 | Loo |
| 2004/0138074 A1 | 7/2004 | Ahmad et al. |
| 2004/0167039 A1 | 8/2004 | Ahmad et al. |
| 2004/0185065 A1 | 9/2004 | Ahmad et al. |
| 2005/0042248 A1 | 2/2005 | Ahmad et al. |
| 2005/0042249 A1* | 2/2005 | Ahmad et al. ............ 424/423 |
| 2005/0066414 A1 | 3/2005 | Yu et al. |
| 2005/0076917 A1 | 4/2005 | Wray et al. |
| 2005/0130522 A1 | 6/2005 | Yang et al. |
| 2005/0141165 A1 | 6/2005 | Stikvoort |
| 2006/0070167 A1 | 4/2006 | Eng et al. |
| 2006/0094608 A1 | 5/2006 | Ahmad et al. |
| 2007/0104766 A1 | 5/2007 | Wang et al. |
| 2007/0287714 A1 | 12/2007 | Ahmad et al. |
| 2008/0210580 A1 | 9/2008 | Harrison |
| 2010/0186751 A1 | 7/2010 | Chuah et al. |

\* cited by examiner

THICKENED SPREADABLE WARMING LUBRICANT

CROSS-REFERENCE TO RELATED APPLICATION

This application is a continuation of U.S. patent application Ser. No. 11/064,284, filed Feb. 23, 2005, which is hereby incorporated by reference in its entirety.

FIELD

The present invention relates to personal lubricants, which are highly spreadable on latex rubber and human skin and which provide a lubricious warming effect upon contact with moisture.

BACKGROUND

Lubricants have been employed for a number of applications, including lubrication of latex condoms and lubrication of skin. More recently, lubricants have been designed to take advantage of the heat that is generated when glycerin or propylene glycol is dissolved in water. Unfortunately, glycerin and propylene glycol do not spread readily on skin and other surfaces and irritate skin after prolonged use, since glycerin extracts water from the skin surface. Addition of thickeners to make the lubricants feel rich severely limits the spreadability of the lubricants. The spreadability of such lubricants is further compromised by the addition of one or more insulating agents, such as honey, isopropyl myristate and/or isopropyl palmitate, which reportedly help to retain the heat of the lubricant (see, e.g., U.S. Pat. App. Pub. Nos. 2004/0138074, 2003/0232090, 2003/0211161 and 2003/0207772, and Int'l App. Pub. Nos. WO 03/092652, WO 03/092651 and WO 09/092,650 discussed below).

U.S. Pat. No. 4,851,434 (the '434 patent) to Decker discloses a non-greasy, nonirritating moisturizer, and compositions containing as the major moisturizing component the di-, tri-, or polyglycol amide or glucamine reaction product with an α-hydroxy-substituted fatty acid, with the formula containing hydrogen or a lower alkyl, preservatives, thickeners, skin-soothing agents, such as allantoin and/or dl-panthenol, and water. The nonirritating moisturizer disclosed in the '434 patent does not produce a warming effect when it contacts body-generated moisture and does not spread spontaneously on human skin.

U.S. Pat. No. 4,952,560 to Kigasawa et al. discloses an ointment base containing a water-soluble protein consisting of gelatin, casein and soybean protein and a monohydric alcohol with a carbon number of 2 to 4 and/or an oleginous substance and additionally containing a wetting agent selected from the group consisting of an alkylene glycol containing 2 to 6 carbon atoms, polyethylene glycol having an average molecular weight of about 200 to 800, glycerin, trimethylolpropane and sorbitol, in a range of 1 to 35 weight % based on the weight of the whole ointment. While the ointment base improves percutaneous absorption of drugs, it is too thick to function as a lubricant.

U.S. Pat. No. 5,441,723 to Simmons discloses a non-toxic hypocompatible biodegradable germicide. The non-toxic hypocompatible biodegradable germicide is effective against a wide range of pathogenic organisms and comprises 65-75 wt % of a monohydric alcohol selected from the group consisting of isopropyl, methyl, ethyl, n-propyl, n-butyl, tert-butyl, allyl, or mixtures thereof, and from about 4% to about 16% by weight of at least one polyhydric alcohol selected from the group consisting of propylene glycol, 1,3 propanediol, 1,2 butanediol, PEG 400, glycerol or 1,4 butanediol, or mixtures thereof in proportion by weight. The monohydric alcohol in the germicide provides the primary disinfecting or killing effect on the pathogenic organisms, while the polyhydric alcohol reduces the surface glaze formed by the monohydric alcohol and the surface tension formed by water or water-based body fluids, thereby enabling the disinfectant/antiseptic to kill pathogenic organisms and act equally effectively on a patient or inanimate surface without deleterious effects, lowers the flash point of the composition, soothes the skin, and slows the rate of evaporation. The germicide is not a lubricant and does not include a warming constituent. In this regard, the polyhydric alcohol, by reducing the rate of evaporation of the monohydric alcohol, essentially cools the surface by evaporative cooling.

U.S. Pat. No. 5,512,289 to Tseng et al. discloses a spermicidal anti-viral lubricant composition containing a water-soluble polymeric gel matrix comprising a hydroxyalkyl cellulose with 2 to 6 carbon atoms; an alkylphenoxypolyethoxyethanol spermicide; and a solubilizing moiety comprising a polyethoxylated non-ionic compound, such as polyethoxylated castor oil. The use of an alkylphenoxypolyethoxyethanol spermicide prevents collapse of the hydroxyalkylcellulose gel. The addition of a solubilizer substantially prevents the collapse of the gel matrix and permits the gel matrix to maintain its properties in the composition. The spermicidal composition can be dispersed by use of a pharmaceutically acceptable vehicle, such as water, alcohols, e.g., ethanol, glycerin, propylene glycol, and mixtures thereof. A typical formulation of the spermicidal lubricant can include water 75.50 wt %, glycerin 17.00 wt %, hydroxyethyl cellulose 1.00 wt %, polyvinyl pyrrolidone 0.90 wt %, carboxymethyl cellulose 1.00 wt %, Nonoxynol-9 spermicide 2.00 wt %, polyethoxylated castor oil 2.00 wt %, methylparaben 0.20 wt %, sorbic acid 0.05 wt %, and citric acid 0.35 wt %. Since glycerin and glycol are already dissolved in water, the lubricant does not provide a warming effect.

U.S. Pat. No. 5,514,698 to Ahmad et al. discloses an antifungal vaginal cream composition. The composition has stable viscosity at human body temperature and comprises about 0.4 to 10.0% of an imidazole antifungal agent (of miconazole, econazole, terconazole, saperconazole, itraconazole, ketoconazole, and clotrimazole), about 1.0% to 5.0% of a fatty acid ester (isopropyl stearate, isopropyl myristate, isopropyl palmitate, and isopropyl laurate), about 1.0% to 25.0% of aliphatic alcohols (cetyl alcohol, stearyl alcohol and propylene glycol), about 2.0% to 5.0% of a surfactant (polysorbate 60 or polysorbate 80), about 0.02% to 0.20% of an antioxidant (butylated hydroxyanisole), a sufficient amount of inorganic base (NaOH or KOH) to adjust the pH range to a value of about 3.0 to 7.0, and water. This vaginal cream is not a lubricant and is expected to maintain its viscosity for prolonged time periods at body temperature. Even though propylene glycol is used in the composition, it is already mixed with water and, therefore, no warming effect takes place when the cream contacts body-generated moisture.

U.S. Pat. No. 5,649,825 to Ratkus discloses a dental root canal bacterialcidal lubricant, which allows the cleaning wires or files to move more freely when removing a nerve from a tooth. The composition reduces packing of tissue and dentin debris within the nerve cavity. This formulation is also resistive to decomposition during cold weather shipping, and includes cetyl alcohol, stearyl alcohol, sodium lauryl sulfate, stearic acid, propylene glycol, methyl paraben, propyl paraben, and butyl paraben in a purified water solution. The lubricant does not provide a warming effect.

U.S. Pat. No. 5,885,591 to Ahmad et al. discloses highly lubricious personal lubricant compositions containing one or more polyhydric alcohols, one or more water-soluble polymers derived from cellulose, water, and, optionally, preservatives and alkali metal or alkaline earth metal bases. These compositions can provide a vehicle for delivering medicaments for contraception and for the treatment and prevention of disease. The personal lubricant composition contains about 30% glycerin, about 5% propylene glycol, about 10% sorbitol, about 0.4% preservative, about 0.4% hydroxyethylcellulose, about 0.01% sodium hydroxide, and about 50% water. The composition has a lubricity of 33 to about 466. The personal lubricant composition attaches to mucous membranes and is not readily washed off. Since the composition already contains water, no heating or warming reaction occurs when the lubricant is applied to the body and the glycerin comes in contact with body-generated moisture.

U.S. Pat. No. 6,139,848 to Ahmad et al. discloses stable personal lubricant compositions containing at least one water-soluble polyhydric alcohol, a water-soluble polymer derived from cellulose, tocopherol or a tocopherol derivative, a nonionic water-soluble or dispersible emulsifier, and water. The lubricious, oily tocopherol or tocopherol derivative is present as an emulsion in the personal lubricant. The emulsifier preferably is a polyalkylene emulsifier chosen from the group consisting of polyoxyethylene sorbitan monostearate, commonly known as Tween 60 or Polysorbate 60, and polyethylene glycol ether of isocetyl alcohol (commonly known as Isoceteth 20 or Arlasolve 200, which is available from ICI Americas, Inc, New Castle, Del.). The water-soluble polyhydric alcohol serves to increase the lubriciousness of the compositions. The water-soluble cellulose-derived polymer serves to impart the desired slipperiness and viscosity to the composition. Water is desired in sufficient quantity to be delivered as moisture to the mucous membranes and to provide consistency and viscosity to the composition. The nonionic surfactants emulsify tocopherol, tocopherol acetate or other tocopherol derivatives into a microemulsion in which the internal or oil phase is reduced to very small globules measuring 2 or less than 2 microns in size. Due to their immensely small size, the emulsion globules do not coalesce and serve to assist in maintaining the homogeneity of the emulsions and to preserve physical stability of the compositions. Since the polyhydric alcohol (glycerin) is already combined with water, no heating or warming reaction occurs when the lubricant is applied to the body.

U.S. Patent Application Publication No. 2001/0039380 to Larson et al. discloses in vivo biocompatible acoustic coupling media comprising polyethylene oxide (PEO), at least one of polyalkylene glycols and polyhydric alcohols, and the balance water. Since water is already added to polypropylene alcohol, the exothermic reaction of mixing has already occurred, and no additional warming occurs when the lubricant is used.

U.S. Patent Application Publication No. 2003/0207772 and International Patent Application Publication No. WO 03/092651 to Ahmad et al. (see also U.S. Pat. App. Pub. No. 2003/0211161 and Int'l Pat. App. Pub. No. WO 03/092652) disclose warming and nonirritating lubricating compositions containing polyhydric alcohols and an insulating agent. The polyhydric alcohol comprises glycerin, alkylene glycol, polyethylene glycol, or a mixture thereof. The alkylene glycol is selected from the group consisting of propylene glycol, butylene glycol and hexylene glycol, whereas the polyethylene glycol is selected from the group consisting of polyethylene glycol 300 and polyethylene glycol 400. The insulating agent is selected from the group consisting of honey, isopropyl myristate and isopropyl palmitate. A warming action is created by the heat released during dissolution of the polyhydric alcohol in water, and the insulating agent retains the heat. The insulating agent is an essential part of the composition of the lubricant, and reduces the spreading capability of the warming lubricant.

U.S. Patent Application Publication No. 2003/0232090 and International Patent Application Publication No. WO 03/092650 to Ahmad et al. disclose warming and nonirritating lubricating compositions. Also disclosed are substantially anhydrous, warming, non-toxic and nonirritating lubricating compositions containing polyhydric alcohols, a hydroxypropylcellulose gelling agent and, alternatively, a pH-adjusting agent for treating fungal and bacterial infections. The polyhydric alcohol comprises glycerin, alkylene glycol, polyethylene glycol, or a mixture thereof. The alkylene glycol is selected from the group consisting of propylene glycol, butylene glycol and hexylene glycol, whereas the polyethylene glycol is selected from the group consisting of polyethylene glycol 300 and polyethylene glycol 400. The insulating agent is selected from the group consisting of honey, isopropyl myristate and isopropyl palmitate. The use of insulating agents reduces the spreading capability of the warming lubricant.

U.S. Patent Application Publication No. 2004/0037911 to Letourneau et al. discloses a genital lubricating composition. The composition comprises (i) fatty acids and/or homeopathic dilutions of plant extracts and (ii) a physiologically acceptable carrier. According to a preferred embodiment, the genital lubricant composition comprises about 0.05% to about 0.5% hemp seed oil and a physiologically acceptable carrier so that it forms a lotion, a cream or a gel. The composition is particularly useful for use as a vaginal moisturizer, or as a personal lubricant for use prior or during sexual intercourse. The fatty acid can be hemp oil, linoleic (C18:2) and/or linolenic (C18:3) acid. The plant extracts include extracts from *Caladium seguinum, Sepia officianalis, Lycopodium clavatum*, and *Onosmodium virginanium*. The exact composition of carrier is not disclosed. This lubricant does not have any polyhydric alcohol and does not produce a warming sensation.

U.S. Patent Application Publication No. 2004/0086575 to Smith discloses anti-viral compositions. The anti-viral compositions contain at least one zinc compound, at least one phenolic antioxidant (and optionally other ingredients), and a pharmaceutical carrier. The zinc compound is selected from the group consisting of zinc, zinc chloride, zinc acetate, zinc citrate, zinc sudoxicam, zinc sulfate, zinc nitrate, zinc carbonate, zinc tartrate, zinc maliate, zinc lactate, zinc aminoacetate, zinc aspartate, zinc glutamate, zinc propionate, zinc oleate, zinc benzoate, zinc gluconate, zinc butyrate, zinc formate, zinc glycerate, zinc glycolate, zinc oxide, zinc ethylenediamine tetraacetate, zinc pentosan polysulfate, zinc oxyacetate, and hydrates. The phenolic antioxidant comprises at least one compound represented by the formula:

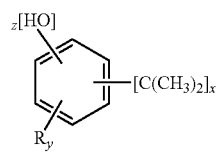

wherein each R is independently an aliphatic hydrocarbon residue, with or without oxygen, comprising 1 to about 12 carbon atoms, x is from 1 to 3, y is from 0 to 3, z is from 1 to 3, and x+y+z is 6 or less. The pharmaceutical carrier comprises at least one of water, alcohol, fatty acids, fatty acid esters, and waxes. The composition does not function as a lubricant.

U.S. Patent Application Publication No. 2004/0138074 to Ahmad et al. discloses substantially anhydrous, warming, non-toxic and nonirritating lubricating compositions containing polyols and preferably an insulating agent. The substantially anhydrous lubricant composition comprises a polyol, which increases in temperature by at least about 5° C., upon exposure to moisture and which has a maximum Energy Release Index of at least about 11 mJ/mg. The polyhydric alcohol is selected from glycerin, alkylene glycol, polyethylene glycol, polypropylene glycol, PEGylated compounds, block copolymers comprising polyalkylene glycol, and their mixtures. The use of insulating agents, such as honey, isopropyl myristate and isopropyl palmitate, reduces the spreading capability of the warming lubricant.

European patent document EP 0636374 to Tseng discloses a spermicidal anti-viral lubricating composition containing an antiviral alkylphenoxypolyethoxyethanol spermicide, a water-soluble polymeric gel matrix, and a solubilizer, which permits the spermicide to be compatible with the gel matrix. Preferably, a polyethoxylated compound, such as polyethoxylated castor oil, is used. There is no warming agent present in the lubricant, since the water-soluble polymer functions as the lubricating agent.

Japanese patent document JP 2292212 to Hans Eke Rennaruto Bidesutoreemu discloses a sterilizable gel. This sterilizing gel comprises a carboxypolymethylene polymer (carboma) and 1-90% polyhydric alcohol for stabilization (e.g., ethylene glycol). The carboma can be sterilized by assistance of the polyhydric alcohol and avoids deterioration of the gel when the gel is sterilized by γ-radiation derived from cobalt 60. This is not a warming gel and polyhydric alcohol is only used to prevent discoloration during γ-radiation.

Japanese patent document JP 2003183115 to Saijo discloses a poikilothermal lubricant. The lubricant may contain ingredients that cause cooling or warming. The warming or cooling ingredient is a dispersant that is not water-soluble and is protected by a polymeric coating. It is unclear what is the nature of the warming agent and what is the mechanism of the warming action.

International Patent Application Publication No. WO 93/18740 to Dunbar discloses a shaving gel. The water-based, non-foaming, shaving gel comprises from 0.05 to 4.0% of a carboxypolymethylene, from 2.00 to 52.0% of a polyhydric alcohol, and, optionally, a silicone derivative, an antipruritic agent, preservative agents, a chelating agent, a neutralizing agent, a solubilizing agent, a UV light-absorbing agent, or a perfume. The preferred polyhydric alcohol is glycerin. The gel is applied directly to dry skin and hair prior to shaving with a razor blade and provides a close, comfortable and well-lubricated shave. The shaving gel does not provide a warming effect.

Notwithstanding the advances in the field of lubricants, and more particularly in the field of warming lubricants and related articles, there remains a need in the art for a warming lubricant that provides effective elastohydrodynamic lubrication as evidenced by improved spreadability on skin, condoms and other surfaces with which it is brought in contact.

SUMMARY

The present invention provides a thickened spreadable warming lubricant that exhibits excellent spreadability and low surface tension and contact angle, thereby providing a well-wetted, uniform, thin layer during skin to skin contact and condom latex film to skin contact. The addition of a thickener to the lubricant provides a rich, creamy composition without adversely affecting spreadability. The thickened spreadable warming lubricant composition has sufficient viscosity to establish easily a thin film on either skin or condom latex film with a film thickness ranging from 0.01 to 0.1 mm. The thickened spreadable warming lubricant composition is substantially anhydrous and comprises a mixture of glycerin with another polyhydric alcohol in the range of 40 wt %-60 wt % each, a non-ionic surfactant in the range of 0.1 to 3 wt %, and a Carbomer thickener in the range of 0.1 to 2.0 wt %. The polyhydric alcohol is preferably propylene glycol, and the non-ionic surfactant is preferably polysorbate 20, polysorbate 40, polysorbate 60 or polysorbate 80. The preferred thickened spreadable warming composition comprises 49.475 wt % glycerin, 49.475 wt % propylene glycol, 0.25 wt % Carbopol 971P NF, 0.30 wt %, of anti-microbial preservative, and 0.5 wt % polyoxyethylene sorbitan monolaurate (polysorbate 20).

The thickened spreadable warming lubricant spreads smoothly with a rich feel and releases heat when mixed with moisture, which can be skin-generated. The temperature rise is optimal when nearly equal volumes of the thickened spreadable warming lubricant and moisture are mixed, since an excess of either moisture or the warming lubricant reduces the temperature rise since the heat released has to heat a larger mass. Therefore, the quantity of the thickened spreadable warming lubricant desirably is limited to the quantity of moisture available during use. Thus, when used with a latex condom, for example, the spreadable warming lubricant desirably coats the surface of the condom as a thin layer. When the interior and exterior surfaces of a latex condom are not coated with a lubricant, there is rubbing between skin and latex, which produces friction and irritation. The presence of a thin, well-spread layer of thickened spreadable warming lubricant minimizes, if not eliminates, friction and irritation and assures uniform heat release, providing a comfortable rich feel and a warming sensation. The thin, well-wetted, thickened, spreadable warming lubricant layer that is in contact with both a condom latex surface and skin or skin and skin, in the case of a stand-alone lubricant, results in an elastohydrodynamic lubricant that functions effectively, reducing friction even when the contacting surfaces deform.

Incorporation of a thickened spreadable warming lubricant onto a condom latex surface, as a uniform coating, in general is difficult to achieve. However, the present inventive thickened spreadable warming lubricant wets latex with a small contact angle. Therefore, the addition of a small quantity of about 0.2-5 ml of spreadable warming lubricant to a condom package results in the migration of the warming lubricant over the internal and external surfaces of the condom. This migration process coats essentially the complete internal and external surfaces of the latex condom with a thin layer of thickened spreadable warming lubricant within a period of approximately a week. Thus, the present inventive spreadable warming lubricant is advantageous in that it enables uniform coating of a lubricant on a condom. Accordingly, the present invention also provides a latex condom, onto which a thickened spreadable warming lubricant has been applied in accordance with such a method.

When the thickened spreadable warming lubricant is used as skin lubricant, the thickened spreadable warming lubricant is applied to the skin in an amount that approximates the available skin moisture. Optionally, moisture can be added to the skin prior to the application of the thickened spreadable warming lubricant. The reaction between moisture and the thickened spreadable warming lubricant results in the release of heat thereby creates a warming sensation. The spreadability of the thickened warming lubricant is essential for this warming effect, since the quantity of moisture available on skin is generally small and the quantity of thickened spreadable warming lubricant applied desirably is matched with this quantity of moisture so as to optimize the warming effect. In the absence of spreadability, the thickened warming lubricant would be concentrated in the area of initial application to the skin, and the desired effects of lubrication and warmth would not be optimized.

DETAILED DESCRIPTION

The present invention provides an improved thickened spreadable warming lubricant that provides and maintains a thin elastohydrodynamic lubricating film between skin and either skin or latex. The lubricant exhibits excellent spreadability due to sufficient viscosity, a low surface tension, and a low contact angle. The lubricant is substantially anhydrous, preferably containing less than about 5 wt % water, more preferably containing less than about 3 wt % water, and most preferably containing less than about 2 wt % water, such as less than about 1 wt % water. Having sufficient viscosity, a film thickness ranging from about 0.01 to 0.10 mm, such as about 0.05 to 0.10 mm, can be achieved on skin or latex rubber.

Accordingly, the present invention provides a thickened spreadable warming lubricant comprising glycerin with another polyhydric alcohol, and a non-ionic surfactant. Preferably, glycerin is present in an amount from about 40 wt % to 60 wt %, the polyhydric alcohol is present in an amount from about 40 wt % to 60 wt %, the non-ionic surfactant is present in an amount from about 0.1 wt % to 3 wt %, and the carbopol thickener 0.1 wt % to 2.0 wt %.

Any suitable polyhydric alcohol can be used. Preferably, the polyhydric alcohol is propylene glycol. Other polyhydric alcohols, such as butylene glycol, hexylene glycol, and polyethylene glycol, are known in the art.

The thickened spreadable warming lubricant has constituents that release heat by exothermic heat of dissolution when mixed with moisture, such as skin-generated moisture. Since skin-generated moisture is generally small in quantity, the quantity of thickened spreadable warming lubricant desirably is small in quantity to take advantage of the exothermic heat release to provide a warming effect. An excessive amount of the thickened spreadable warming lubricant in the presence of a small amount of skin-generated moisture results in only a small temperature rise resulting in a minimal warming effect. The small quantity of thickened spreadable warming lubricant can only be effective if it creates a stable elastohydrodynamic film over the skin or between skin and a latex article.

Polyhydric alcohols react with water to release heat by an exothermic dissolution reaction. This effect is well-known and documented in several chemistry textbooks, including supplier literature of Dow Chemical Company (Midland, Mich.). Any of the polyhydric alcohols, including glycerin, propylene glycol, butylene glycol, hexylene glycol, and polyethylene glycol, exhibit this exothermic reaction. The spreadable warming lubricant has glycerin and a polyhydric alcohol, preferably propylene glycol, mixed in an appropriate ratio to ensure that the viscosity of the mixture provides sufficient lubricating properties. The higher the viscosity, the higher is the drag when the contacting surfaces are moved with respect to one another. In addition, higher viscosity compositions tend to form thick lubricating films, since gravitational forces are inadequate to form a thin film, whereas lower viscosity compositions run off easily, forming very thin lubricating films.

The viscosity of a glycerin-propylene mixture as a function of composition is shown in Table 1 below. Propylene glycol is too low to be useful as a lubricant, while glycerin has too high a viscosity to produce evenly a thin lubricating film. Table 1 also documents the warming effect of the lubricant composition in three trials. Propylene glycol provides the largest warming effect, while glycerin produces the smallest warming effect.

TABLE 1

| | wt % Propylene Glycol | | | | | | | | |
|---|---|---|---|---|---|---|---|---|---|
| | 0 | | | 50 | | | 100 | | |
| | wt % Glycerin 99.7% | | | | | | | | |
| | 100 | | | 50 | | | 0 | | |
| | Test No | | | | | | | | |
| | 1 | 2 | 3 | 1 | 2 | 3 | 1 | 2 | 3 |
| $T_{max}$ (° C.) | 35.7 | 35.8 | 35.8 | 37.2 | 37.5 | 37.6 | 38.5 | 38.1 | 38.5 |
| $T_b$ (° C.) | 23.8 | 23.8 | 24.1 | 24.1 | 24.0 | 24.0 | 23.8 | 24.0 | 24.1 |
| $\Delta T_{sample} = T_{max} - T_b$ (° C.) – $T_{sf}$ | 5.7 | 5.8 | 5.5 | 6.9 | 7.3 | 7.4 | 8.5 | 7.9 | 8.2 |
| Avg warming, $\Delta T$ (° C.) | | 5.7 | | | 7.2 | | | 8.2 | |
| Viscosity (at 25° C.) | | ~565.5 cps | | | ~140 cps | | | ~32 cps | |

$T_b$ = room temperature of sample.
$T_{max}$ = highest temperature of sample upon mixing with equal amount of water at 37° C.
Tsf = 6.2° C., inherent effect of mixing water at 37° C. with water at room temperature
$\Delta T_{sample}$ = increase in temperature of sample after mixing with equal amount of water at 37° C.
cps = centipoises The thickened spreadable warming lubricant must wet the surfaces in question and must have a low contact angle. This requirement is even more important when the surfaces in contact are deformable and the adhesion of the film to the surface needs to be better, thus demanding even a smaller contact angle. If the contact angle is large, the lubricating fluid film disrupts creating islands, which are physically separated, and rubbing now occurs between skin and skin or between skin and latex, both of which are high friction coefficient couples providing skin irritation. Improved wetting of a glycerin-propylene glycol mixture is accomplished by addition of 0.1 to 3 percent of non-ionic surfactants.

Non-ionic surfactants, as the name implies, means no ionic constituents are present. They are "ionically" inert. A vast majority of all non-ionic detergents are condensation products or ethylene oxide with a hydrophobe. This group of detergents is enormous, and the permutations endless. They would be the single largest group of all surfactants. The book titled 'Nonionic Surfactants: Organic Chemistry' by: Nico M. van Os, ed. ISBN: 0 824 79997 6 Publisher: Marcel Dekker Copyright: 1998 discusses a number of non-ionic surfactants, including polyoxyethylene alkylphenols, alcohols, esters of fatty acids, mercaptans, and alkylamines, nonionic surfactants containing an amide group, and polyol ester surfactants, and the book is specifically incorporated herein by reference. Dow Corporation markets a number of non-ionic surfactants under the trade name 'DOWFAX'. These polyethylene glycol formulations provide superior softening, conditioning, and skin-smoothing characteristics, since polyglycols dissolve or are compatible and miscible in various organic liquids.

Polysorbate compositions are also non-ionic surfactants and are available as polysorbate—20, 40, 60, 65 and 80. They are polyoxyethylene sorbitan monoesters (PS) of the general formula:

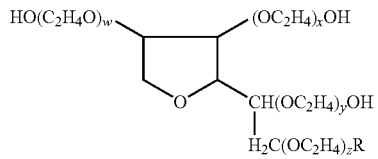

wherein R is laureate, palmitate, stearate or oleate and each of w, x, y and z is independently 1 or 2; or each of w, x, y and z is independently less than or equal to 17, and the sum of w, x, y and z is 20. Polysorbate-20 is polyoxyethylenesorbitan monolaurate, CAS #9005-64-5, with a chemical composition of sorbitan mono-9-octadecenoate poly(oxy-1,1-ethanediyl). Polysorbate 40 is polyethylene glycol sorbitan monopalmitate, polyoxyethylene sorbitanmonopalmitate, CAS#9005-66-7, Polysorbate 60 is polyethylene glycol sorbitan monostearate, polyoxyethylene sorbitanmonostearate, CAS #9005-67-8, and Polysorbate 80 is polyoxyethylenesorbitan monooleate, CAS#9005-65-6.

Optionally, anti-microbial preservatives can be used in the thickened spreadable warming lubricant. Typical anti-microbial preservatives include, but are not limited to, para-benzoates, parahydroxy benzoates and their esters, methyl paraben and propyl paraben. Tables 2 A, B and C show the effect of the addition of polysorbate 20 to warming lubricant compositions containing propylene glycol and glycerin on drop diameter, when a fixed volume of liquid is applied to a substrate, including glass, latex condom film and skin, and the corresponding contact angle. This contact angle is determined by dropping a fixed volume of 25 µl of lubricant mixture using a microsyringe on a flat substrate of glass, condom latex film or skin, respectively, and measuring the diameter of the spread of the warming lubricant as a function of time. The contact angle is calculated using a well-known formula (Roberts et al., Surface Treatments to Reduce Friction—Rubber Chemistry and Technology 63:722 (1990)) as shown below, wherein D is the diameter of the lubricant and V is the volume of the warming liquid:

$$\frac{D^3}{V} = \frac{24\sin^3\theta}{\pi(2 - 3\cos\theta + \cos^3\theta)}$$

TABLE 2A

Substrate: GLASS
Average Base Diameter of Drop (mm) & Contact Angle (degrees)

| Lapse time | Drop Vol. | 50 wt % Propylene Glycol, 50% glycerin | | 49.50 wt % Propylene Glycol, 49.5 wt % glycerin, 0.5 wt % PS20 | | Glycerin | | Glycerin, 0.5 wt % PS20 | | Propylene Glycol | | Propylene Glycol, 0.5 wt % PS20 | |
|---|---|---|---|---|---|---|---|---|---|---|---|---|---|
| (mins) | (µL) | mm | deg | mm | deg | mm, | deg | mm, | deg | mm | deg | mm | deg |
| 1 | 25 | 7.0 | 39 | 8.0 | 27.4 | 6.0 | 56.4 | 6.5 | 41.5 | 7.0 | 39 | 8.0 | 27.4 |
| 10 | 25 | 7.0 | 39 | 9.5 | 16.8 | 6.0 | 56.4 | 8.0 | 27.4 | 8.0 | 27.4 | 10.0 | 14.4 |
| 60 | 25 | 7.5 | 32.7 | 10.5 | 12.5 | 7.0 | 39 | 10.0 | 14.4 | 8.0 | 27.4 | 11.5 | 9.5 |
| 135 | 25 | 7.5 | 32.7 | 12.0 | 8.4 | 7.5 | 32.7 | — | — | 8.0 | 27.4 | 12.5 | 7.4 |
| 300 | 25 | 8.0 | 27.4 | 12.5 | 7.4 | 8.0 | 27.4 | 12.0 | 8.4 | 8.5 | 23.1 | 13.5 | 5.9 |

TABLE 2B

Substrate: CONDOM LATEX FILM
Average Base Diameter of Drop (mm) & Contact Angle (degrees)

| Lapse time | Drop Vol. | 50 wt % Propylene Glycol, 50 wt % glycerin | | 49.50 wt % Propylene Glycol, 49.5 wt % glycerin, 0.5 wt % PS20 | | Glycerin | | Glycerin, 0.5 wt % PS20 | | Propylene Glycol | | Propylene Glycol, 0.5 wt % PS20 | |
|---|---|---|---|---|---|---|---|---|---|---|---|---|---|
| (mins) | (µL) | mm | deg | mm | deg | mm | Deg | mm | deg | mm | deg | mm | deg |
| 1 | 25 | 5.0 | 78.9 | 6.0 | 56.4 | 5.0 | 78.9 | 6.0 | 56.4 | 6.0 | 56.4 | 7.0 | 39 |
| 10 | 25 | 5.0 | 78.9 | 7.0 | 39 | 5.0 | 78.9 | 6.0 | 56.4 | 6.0 | 56.4 | 7.0 | 39 |

TABLE 2B-continued

Substrate: CONDOM LATEX FILM
Average Base Diameter of Drop (mm) & Contact Angle (degrees)

| Lapse time (mins) | Drop Vol. (μL) | 50 wt % Propylene Glycol, 50 wt % glycerin | | 49.50 wt % Propylene Glycol, 49.5 wt % glycerin, 0.5 wt % PS20 | | Glycerin | | Glycerin, 0.5 wt % PS20 | | Propylene Glycol | | Propylene Glycol, 0.5 wt % PS20 | |
|---|---|---|---|---|---|---|---|---|---|---|---|---|---|
| | | mm | deg | mm | deg | mm | Deg | mm | deg | mm | deg | mm | deg |
| 60 | 25 | 5.0 | 78.9 | 9.0 | 19.6 | 5.5 | 67.5 | 8.5 | 23.1 | 6.0 | 56.4 | 8.0 | 27.4 |
| 135 | 25 | 6.0 | 56.4 | 9.0 | 19.6 | 6.5 | 41.5 | 9.0 | 19.6 | 7.0 | 39 | 9.0 | 19.6 |
| 300 | 25 | 6.0 | 56.4 | 9.0 | 19.6 | 7.0 | 39 | 10.0 | 14.4 | 7.5 | 32.7 | 9.5 | 16.8 |

TABLE 2C

Substrate: SKIN ON ARM
Average Base Diameter of Drop (mm) & Contact Angle (degrees)

| Lapse time (mins) | Drop Vol. (μL) | 50 wt % Propylene Glycol, 50 wt % glycerin | | 49.75 wt % Propylene Glycol 49.75 wt % glycerin, 0.5 wt % PS20 | | Glycerin | | Glycerin, 0.5 wt % PS20 | | Propylene Glycol | | Propylene Glycol, 0.5 wt % PS20 | |
|---|---|---|---|---|---|---|---|---|---|---|---|---|---|
| | | mm | deg | mm | deg | mm | deg | mm | deg | mm | deg | mm | deg |
| 1 | 25 | 6.0 | 56.4 | 6.5 | 41.5 | 5.0 | 78.9 | 6.0 | 56.4 | 7.0 | 39 | 7.0 | 39 |
| 5 | 25 | 7.5 | 32.7 | 10.5 | 12.5 | 5.5 | 41.5 | 8.0 | 27.4 | 8.0 | 27.4 | 8.0 | 27.4 |

The contact angle measured by this spreading drop measurement compares well with the Kruss Contact Angle measurement as shown in Table 2D below. Skin tests could not be successfully conducted using the Kruss contact angle meter, since the applied drop spreads too rapidly.

TABLE 2D

Substrate CONDOM LATEX FILM
Contact Angle (degrees)

| Lapsed time (mins) | 50 wt % Propylene Glycol, 50 wt % glycerin (deg) | 49.75 wt % Propylene Glycol 49.75 wt % glycerin, 0.5 wt % PS20 (deg) | Glycerin (deg) |
|---|---|---|---|
| 1 | 85.06 | 57.45 | 84.86 |
| 5 | 88.14 | 50.75 | 82.9 |
| 10 | 86.26 | 48.48 | 79.25 |

The surface tensions of the warming lubricants were measured and are shown below in Table 2E.

TABLE 2E

Surface Tension (N/m)

| 50 wt % Propylene Glycol, 50 wt % glycerin (N/m) | 49.75 wt % Propylene Glycol 49.75 wt % glycerin, 0.5 wt % PS20 (N/m) | Glycerin (N/m) | Glycerin, 0.5 wt % PS20 (N/m) | Propylene Glycol (N/m) | Propylene Glycol, 0.5 wt % PS20 (N/m) |
|---|---|---|---|---|---|
| 0.046 | 0.037 | 0.067 | 0.036 | 0.0385 | 0.03825 |

It is, therefore, very clear that adding 0.5 wt % of polysorbate 20 increases the spread diameter of the lubricant, and decreases contact angle and surface tension in all cases. The combination of appropriate lubricant viscosity and lubricant spreading capability generates an effective warming lubricant as demonstrated by the warming lubricant composition having 49.75 wt % propylene glycol, 49.75 wt % glycerin, and 0.5 wt % polysorbate 20.

Even though this specific composition is shown in Tables 2A-C, the propylene glycol can be in the range of 40 wt % to 60 wt %, glycerin can be in the range of 40 to 60 wt %, and polysorbate 20 or other non-ionic surfactant can be in the range of 0.1 to 3 wt %. The viscosity of glycerin propylene glycol is relatively stable in this compositional range, and polysorbate 20 and other non-ionic surfactants are effective in improving the contact angle.

The warming lubricant can be used as a skin lubricant wherein a small drop of 25 μl volume of the warming lubricant is applied over skin and rubbed. Any skin-generated moisture quickly produces a warming effect as the warming lubricant combines with moisture. The warming lubricant is highly spreadable and produces a soothing effect.

The spreadable warming lubricant can be applied to a condom latex surface. Due to its enhanced spreading character, the warming lubricant spreads over the internal and external surface of the condom latex. The utility of a lubricated condom is related to distribution of the lubricating agent on the condom surface, since this lubrication is what prevents irritation. Any lubricant that does not spread well has bare spots, where latex condom surface rubs directly on skin and creates increased friction, stickiness and irritation. In order to quantify this effect, a small amount of spreadable warming lubricant was applied on the external surface of a condom, and the spreading of the warming lubricant was measured. The results are shown below in Table 2F.

TABLE 2F

Migration Up Condom Shaft (weeks)

| | Time | | | | | |
|---|---|---|---|---|---|---|
| | 1 week | 2 weeks | 3 weeks | 1 week | 2 weeks | 3 weeks |
| Propylene glycol wt % | 0 | 0 | 0 | 50 | 50 | 50 |
| Glycerin wt % | 100 | 100 | 100 | 50 | 50 | 50 |
| Migration up condom shaft after 1, 2, 3 wks (cm)* | 5 | 4.5 | 5.7 | 13.3 | 18.5 | 18.5 |
| Migration up condom shaft with 0.5 wt % Polysorbate 20 after 1, 2, 3 wks (cm) | 15 | 15.5 | 16.8 | 16.8 | 17.5 | 17 |

The 50 wt %-50 wt % mixture of glycerin and propylene glycol has a higher migration distance up the condom shaft as compared to pure glycerin. When polysorbate 20 is added to the lubricant, both glycerin and the 50%-50 wt % mixture of glycerin and propylene glycol show improvement in the migration distance of the lubricant up the condom shaft, particularly within one week.

A number of compounds are available for increasing the viscosity of the warming lubricant to produce effectively a thickened, spreadable, warming lubricant. The thickener has to be mixable in a glycerin- and polypropylene glycol-based lubricant composition and must be compatible with polar solvents. Unfortunately, most of the thickeners generally used also limit the spreadability of the lubricant. Several cellulose-based thickeners, for example, limit spreadability. Compatible thickeners include, but are not limited to, polyacrylates that are cross-linked or non-cross-linked polysaccharides. We have found to our surprise that the addition of Carbomer (Carbopol 971P NF resin) to a warming lubricant provides higher viscosity without limiting spreadability. Other carbomer compositions are detailed in the Carbopol resin handbook, a Noveon (Cleveland, Ohio) publication, which is hereby incorporated by reference.

The effect of the addition of thickener to a spreadable warming lubricant was investigated by comparing two compositions, one with and the other without polysorbate-20 non-ionic surfactant. These compositions are shown in Table 3 below.

TABLE 3

Thickened Spreadable Warming Lubricant Composition

| Constituent | Composition A wt % | Composition B wt % |
|---|---|---|
| Glycerin | 49.725 | 49.475 |
| Propylene Glycol | 49.725 | 49.475 |

TABLE 3-continued

Thickened Spreadable Warming Lubricant Composition

| Constituent | Composition A wt % | Composition B wt % |
|---|---|---|
| Carbopol | 0.25 | 0.25 |
| Antimicrobial Preservative | 0.3 | 0.3 |
| Polysorbate 20 | 0.0 | 0.5 |

The viscosity of the composition A is 1450 cps as compared to that of composition B, which is 1425 cps. Therefore, the addition of polysorbate did not deteriorate the viscosity of the composition. Note that the viscosity of the thickened spreadable warming lubricant was much greater than that of the spreadable warming lubricant without the addition of thickener as reported in Table 1. The increased viscosity of the composition provided a richer, creamy lubricant.

The spreadability of the thickened spreadable warming lubricant was next measured on glass substrate and flat latex substrate, and the results are reported in Tables 4A through 4C. The surface tension of the thickened spreadable warming lubricant was measured using a surface tensometer, and the temperature was controlled to 23° C.±1° C. The results are reported in Table 4D.

TABLE 4A

Substrate: GLASS
Average Base Diameter of Drop (mm) & Contact Angle (degrees)

| | Drop Volume | Composition A | | Composition B | |
|---|---|---|---|---|---|
| Lapsed time | (µL) | mm | deg | mm | Deg |
| 1 | 25 | 7.0 | 39.0 | 7.0 | 39.0 |
| 10 | 25 | 7.0 | 39.0 | 8.5 | 23.1 |
| 60 | 25 | 7.0 | 39.0 | 10.0 | 14.4 |

TABLE 4B

Substrate: CONDOM LATEX FILM
Average Base Diameter of Drop (mm) & Contact Angle (degrees)

| | Drop Volume | Composition A | | Composition B | |
|---|---|---|---|---|---|
| Lapsed time | (µL) | mm | deg | mm | Deg |
| 1 | 25 | 5.0 | 78.9 | 5.5 | 67.5 |
| 10 | 25 | 5.0 | 78.9 | 7.0 | 39.0 |
| 60 | 25 | 6.0 | 56.4 | 8.0 | 27.4 |

TABLE 4C

Substrate: SKIN
Average Base Diameter of Drop (mm) & Contact Angle (degrees)

| Lapsed time | Drop Volume (µL) | Composition A mm | Composition A deg | Composition B mm | Composition B Deg |
|---|---|---|---|---|---|
| 1 | 25 | 5.5 | 67.5 | 6.0 | 56.4 |
| 5 | 25 | 6.0 | 56.4 | 9.0 | 19.6 |

TABLE 4D

Surface Tension (N/m)

| Composition A (N/m) | Composition B (N/m) |
|---|---|
| 0.04600 | 0.03650 |

The addition of polysorbate 20 non-ionic surfactant improved the spreadability of the thickened warming lubricant. Comparison of data in Tables 4B and 2B and Tables 4C and 2C clearly shows that the addition of thickener did not significantly reduced the spreadability of thickened warming lubricant. For example, Tables 4B and 2B show that, at 10 minutes of time lapse, the thickened warming lubricant had a spreadability of 7 mm, while the warming lubricant without the thickener had essentially the same spreadability of 7 mm. Comparison of Tables 4C and 2C shows that spreadability of the thickened spreadable warming lubricant is 9.0 mm as compared to 10.5 mm for a warming lubricant without the thickener at a lapse time of 5 minutes. Therefore, the addition of the thickener provided a rich feel to the lubricant, without limiting its spreadability on skin or latex.

The mode of application of the thickened spreadable warming lubricant in condoms includes dropping a measured quantity of warming lubricant consistent with the skin-generated moisture. Since the skin-generated moisture is generally in the range of 0.2 to 5 ml, the quantity of the thickened warming lubricant desirably is less than 5 ml. This small quantity of the thickened warming lubricant has to be spread all over the internal and external surface of the condom latex to provide effective lubrication and warming effect. During packaging of a condom, the measured quantity of thickened spreadable warming lubricant is added, and the spreading effect is relied on to disperse the lubricant across the internal and external surfaces of the condom.

When the thickened spreadable warming lubricant is used as skin lubricant, the lubricant is applied to the skin in an amount that approximates the available skin moisture. The lubricant has a rich feel due to its creamy texture. Optionally, moisture can be added to the skin prior to the application of the thickened spreadable warming lubricant. The reaction between moisture and the thickened spreadable warming lubricant results in the release of heat, thereby creates a warming sensation. The spreadability of the thickened warming lubricant is essential for this warming effect, since the quantity of moisture available on skin is generally small and the quantity of spreadable warming lubricant applied desirably is matched with this quantity of available moisture so as to optimize the warming effect. In the absence of spreadability, the warming lubricant would be concentrated in the area of initial application to the skin, and the desired effects of lubrication and warmth would not be optimized. The combination of suitable viscosity, low surface tension and contact angle with respect to human skin results in spreading of the warming lubricant on the skin so as to provide an optimal, soothing warming effect.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A method of using a lubricant, the method comprising:
    placing an amount of a thickened spreadable warming lubricant on moist skin, the thickened spreadable warming lubricant comprising glycerin, a polyhydric alcohol, a non-ionic surfactant, and a thickener that comprises carbomer;
    forming a thickness of the lubricant in the range of 0.01 to 0.1 mm on the moist skin due to the spreadable nature of the lubricant; and
    generating heat upon contact of the lubricant with the moist skin.

2. The method of claim 1, wherein the amount is in the range of 0.2 to 5 mL.

3. The method claim 1, wherein a drop of the lubricant in the amount of 25 µL spreads to a diameter of at least 6 mm after about 1 minute on the moist skin.

4. The method of claim 1, wherein a contact angle between the lubricant and the moist skin is about 56° or less after about 1 minute on the moist skin.

5. The method of claim 1, wherein the heat results in a temperature rise of at least 6° C.

6. The method of claim 1, wherein the lubricant comprises glycerin in an amount in the range of 40 wt % to 60 wt %, the polyhydric alcohol in an amount in the range of 40 wt % to 60 wt %, the non-ionic surfactant in an amount in the range of 0.1 wt % to 3 wt %, and the thickener in an amount in the range of 0.1% wt to 2.0 wt %.

7. The method of claim 1, wherein the lubricant consists essentially of 48-52 wt % glycerin, 48-52 wt % propylene glycol, 0.1-2.0 wt % carbomer thickener, 0.1-1.0 wt % polyoxyethylene sorbitan monolaurate, and a preservative.

8. A thickened spreadable warming lubricant comprising:
    a first polyhydric alcohol having a first viscosity in an amount in the range of 40 wt % to 60 wt %;

a second polyhydric alcohol having a second viscosity in an amount in the range of 40 wt % to 60 wt %;

a non-ionic surfactant in an amount in the range of 0.1 wt % to 3 wt %; and a thickener that comprises carbomer, the carbomer in an amount in the range of 0.1 wt % to 2 wt %, wherein the thickened spreadable warming lubricant is substantially anhydrous, produces a thin lubricious layer on skin, and produces a warming effect upon contact with moisture.

9. The thickened spreadable warming lubricant of claim 8, wherein the first polyhydric alcohol comprises glycerin.

10. The thickened spreadable warming lubricant of claim 8, wherein the second polyhydric alcohol comprises polypropylene glycol.

11. The thickened spreadable warming lubricant of claim 8, wherein the non-ionic surfactant is a polyoxyethylene sorbitan monoester.

12. The thickened spreadable warming lubricant of claim 8, wherein the carbomer comprises a polyacrylate.

13. The thickened spreadable warming lubricant of claim 8 being provided in a package having a volume in the range of 0.2 to 5 mL.

14. The thickened spreadable warming lubricant of claim 8 wherein the first viscosity of the first polyhydric alcohol measured at 25° C. is in the range of 500 to 600 centipoise.

15. The thickened spreadable warming lubricant of claim 8 wherein the second viscosity of the second polyhydric alcohol measured at 25° C. is in the range of 25 to 40 centipoise.

16. The thickened spreadable warming lubricant of claim 8 wherein the viscosity of the lubricant measured at 25° C. is at least 1400 centipoise.

17. The thickened spreadable warming lubricant of claim 8 wherein the viscosity of the lubricant measured at 25° C. is in the range of 1400 to 1450 centipoise.

18. A thickened spreadable warming lubricant comprising:

a first polyhydric alcohol, in an amount in the range of 48 wt % to 52 wt %;

a second polyhydric alcohol, in an amount in the range of 48 wt % to 52 wt %;

a non-ionic surfactant in an amount in the range of 0.1 wt % to 1 wt %; and a thickener in an amount in the range of 0.1 wt % to 2 wt %, wherein the thickened spreadable warming lubricant is substantially anhydrous, produces a thin lubricious layer on skin, and produces a warming effect upon contact with moisture, the viscosity of the lubricant measured at 25° C. is at least 1400 centipoise, a drop of the lubricant in the amount of 25 µL spreads to a diameter of at least 6 mm after about 1 minute on the moist skin, and a contact angle between the lubricant and the moist skin is about 56° or less after about 1 minute on the moist skin.

19. The thickened spreadable warming lubricant of claim 18 wherein the viscosity of the lubricant measured at 25° C. is in the range of 1400 to 1450 centipoise.

20. The thickened spreadable warming lubricant of claim 19 wherein the wherein the lubricant consists essentially of 48-52 wt % the first polyhydric alcohol having a viscosity in the range of 500 to 600 centipoise as measured at 25° C., 48-52 wt % the second polyhydric alcohol having a viscosity in the range of 25 to 40 centipoise as measured at 25° C., 0.1-2.0 wt % thickener, 0.1-1.0 wt % non-ionic surfactant, and a preservative.

* * * * *